United States Patent [19]

Davies et al.

[11] Patent Number: 4,659,718

[45] Date of Patent: Apr. 21, 1987

[54] ANTIHYPERTENSIVE 3-TETRAZOYL-4-QUINOLONES

[75] Inventors: Roy V. Davies; Richard D. Green, both of Nottinghamshire, England

[73] Assignee: The Boots Company Plc, England

[21] Appl. No.: 749,015

[22] Filed: Jun. 26, 1985

Related U.S. Application Data

[63] Continuation of Ser. No. 642,060, Aug. 20, 1984, abandoned.

[30] Foreign Application Priority Data

Aug. 20, 1983 [GB] United Kingdom ............... 8322470
May 25, 1984 [GB] United Kingdom ............... 8413535

[51] Int. Cl.$^4$ ..................... A61K 31/41; C07D 401/04
[52] U.S. Cl. ..................... 514/312; 546/153; 544/128; 548/252
[58] Field of Search ............... 546/153; 514/312

[56] References Cited

U.S. PATENT DOCUMENTS

| | | | |
|---|---|---|---|
| 4,035,368 | 7/1977 | Erickson | 546/153 |
| 4,259,437 | 3/1981 | Webb | 548/254 |
| 4,302,460 | 11/1981 | Davies | 546/155 |
| 4,442,109 | 4/1984 | Davies | 546/153 |
| 4,474,787 | 10/1984 | Cairns | 546/89 |

FOREIGN PATENT DOCUMENTS 104018A 9/1983 European Pat. Off. .
120483A 10/1984 European Pat. Off. .
50106975 8/1975 Japan .

OTHER PUBLICATIONS

Erickson et al., J. of Medicinal Chemistry, 22(7), p. 816 (1979).
Gilis et al., Eur. J. Med. Chem., 15, No. 6, pp. 499–502 (1980).
Kim. J. Hetercyclic Chem., 18, pp. 1393–1397 (1981).

Primary Examiner—Christine M. Nucker
Assistant Examiner—Robert Benson
Attorney, Agent, or Firm—Jacobs & Jacobs

[57] ABSTRACT

Novel quinolones of formula I

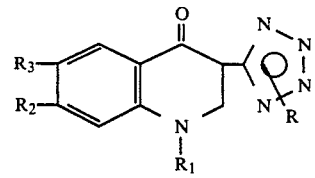

and pharmaceutically acceptable acid addition salts thereof in which the dotted line between positions 2 and 3 of the quinolone ring represents an optional bond, R is hydrogen, 1-methyl or 2-lower alkyl; $R_1$ is lower alkyl; $R_2$ is hydrogen, halo, lower alkyl, lower alkoxy, trifluoromethyl, cyano, difluoromethoxy, methylsulphinyl, phenylsulphinyl or the group —$NR_4R_5$ or the N-oxide thereof wherein $R_4$ and $R_5$, which may be the same or different, are lower alkyl or, together with the nitrogen atom to which they are attached form a pyrrolidino, piperidino or morpholino radical; and $R_3$ is hydrogen, fluoro, lower alkyl or lower alkoxy provided that, when $R_3$ is lower alkoxy, $R_2$ is other than lower alkoxy have utility as antihypertensive agents. Processes for preparing the quinolones and pharmaceutical compositions containing them are disclosed.

29 Claims, No Drawings

ANTIHYPERTENSIVE 3-TETRAZOYL-4-QUINOLONES

CROSS-REFERENCE

This is a continuation of Ser. No. 642,060, filed Aug. 20, 1984, now abandoned.

This invention relates to novel quinolone compounds with therapeutic activity as antihypertensive agents, to therapeutic compositions containing the quinolones and to processes for preparing the quinolones.

The present invention provides novel quinolones of the formula I

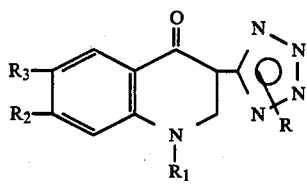

and pharmaceutically acceptable acid addition salts thereof, in which the dotted line between positions 2 and 3 of the quinolone ring represents an optional bond, R is hydrogen, 1-methyl or 2-lower alkyl; $R_1$ is lower alkyl; $R_2$ is hydrogen, halo, lower alkyl, lower alkoxy, trifluoromethyl, cyano, difluoromethoxy, methylsulphinyl, phenylsulphinyl or the group $-NR_4R_5$ or the N-oxide thereof wherein $R_4$ and $R_5$, which may be the same or different, are lower alkyl or, together with the nitrogen atom to which they are attached, form a pyrrolidino, piperidino or morpholino radical; and $R_3$ is hydrogen, fluoro, lower alkyl or lower alkoxy provided that, when $R_3$ is lower alkoxy, $R_2$ is other than lower alkoxy.

The term "lower" signifies a radical with 1–4 carbon atoms. Any alkyl chain in the above-mentioned radicals may be straight or branched. Examples of such radicals include methyl, ethyl, propyl, isopropyl, butyl, secondary butyl, tertiary butyl, methoxy, ethoxy, propoxy, isopropoxy and methylsulphinyl. The radical R is preferably methyl situated at the 1-position of the tetrazol-5-yl radical. The radical $R_1$ is preferably methyl. The term "halo" signifies fluoro, chloro or bromo.

It will be appreciated by those skilled in the art that, in formula I, the moiety

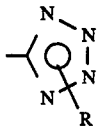

represents a 1H- or 2H-tetrazol-5-yl radical in which R is linked to a nitrogen atom, i.e. R is situated at the 1- or 2-position of the ring.

It will also be appreciated that, when the optional 2,3-bond is absent, the compounds of formula I have a chiral centre and thus exist in two enantiomeric forms. The present invention includes both enantiomers and mixtures thereof.

We have found that the compounds of formula I have valuable antihypertensive activity. The compounds reduce blood pressure when administered to hypertensive mammals.

The compounds of formula I are weak bases and form acid addition salts with strong acids, for example hydrochloric acid. It will be appreciated that such salts, provided they are pharmaceutically acceptable, may be used in therapy in place of the corresponding compounds of formula I. Such salts are prepared by reacting the compound of formula I with a suitable acid in a conventional manner.

The present invention provides pharmaceutical compositions which comprise a compound of formula I or a pharmaceutically acceptable acid addition salt thereof together with a pharmaceutically acceptable carrier.

As used hereinafter, the term "active compound" denotes a quinolone of general formula I, or a pharmaceutically acceptable acid addition salt thereof in therapeutic use, the active compound may be administered orally, rectally, parenterally or topically, preferably orally. Thus the therapeutic compositions of the present invention may take the form of any of the known pharmaceutical compositions for oral, rectal, parenteral or topical administration. Pharmaceutically acceptable carriers suitable for use in such compositions are well known in the art of pharmacy. The compositions of the invention suitably contain 0.1–90% by weight of active compound. The compositions of the invention are generally prepared in unit dosage form.

Compositions for oral administration are the preferred compositions of the invention and these are the known pharmaceutical forms for such administration, for example tablets, capsules, syrups and aqueous or oily suspensions. The excipients used in the preparation of these compositions are the excipients known in the pharmacist's art. Tablets may be prepared by mixing the active compound with an inert diluent such as calcium phosphate in the presence of disintegrating agents, for example maize starch, and lubricating agents, for example magnesium stearate, and tableting the mixture by known methods. Such tablets may, if desired, be provided with enteric coatings by known methods, for example by the use of cellulose acetate phthalate. Similarly capsules, for example hard or soft gelatin capsules, containing the active compound with or without added excipients, may be prepared by conventional means and, if desired, provided with enteric coatings in a known manner. Enteric coated compositions of the invention may be advantageous, depending on the nature of the active compound. The tablets and capsules may conveniently each contain 1–500 mg of the active compound. Other compositions for oral administration include, for example, aqueous suspensions containing the active compound in an aqueous medium in the presence of a non-toxic suspending agent such as sodium carboxymethylcellulose, and oily suspensions containing a compound of the present invention in a suitable vegetable oil, for example arachis oil.

Compositions of the invention suitable for rectal administration are the known pharmaceutical forms for such administration, for example, suppositories with cocoa butter or polyethylene glycol bases.

Compositions of the invention suitable for parenteral administration are the known pharmaceutical forms for such administration, for example, sterile suspension in aqueous and oily media or sterile solutions in a suitable solvent.

Compositions for topical administration may comprise a matrix in which the active compound is dispersed so that the compound is held in contact with the skin in order to administer the active compound transdermally. Alternatively the active compound may be dispersed in a cream or ointment base.

In some formulations it may be beneficial to use the compounds of the present invention in the form of particles of very small size, for example, as obtained by fluid energy milling.

In the compositions of the present invention the active compound may, if desired, be associated with other compatible pharmacologically active ingredients, for example a β-blocker such as propranolol, oxprenolol or timolol, or a diuretic such as bendrofluazide.

The therapeutic activity of the compounds of general formula I has been demonstrated by means of tests on standard laboratory animals. Such tests include, for example, the oral administration of the compounds to a strain of spontaneously hypertensive rat and the intra-duodenal administration of compounds to a stain of normotensive rat. Thus the compounds of formula I are useful for reducing blood pressure in hypertensive mammals. A suitable dose for enteral administration to mammals, including man, is generally within the range 0.1–25 mg/kg/day, more usually 0.5–10 mg/kg/day, given in single or divided doses. For parenteral administration, a suitable dose is generally within the range 0.01–2.5 mg/kg/day, especially 0.05–1.0 mg/kg/day. Oral administration is preferred.

We have found that the compounds of formula I are vasodilators. Accordingly the compounds are indicated for use in the treatment of ischaemic heart disease and heart failure in mammals, including man. Suitable dosages are those given above. A typical compound of the present invention, 1-methyl-3-(1-methyl-1H-tetrazol-5-yl)-4-quinolone, has been found to have a vasodilating action on both venous and arterial beds. This pharmacological effect is of particular value in the treatment of ischaemic heart disease and heart failure.

The compounds of formula I in which the optional 2,3-bond is present, R is 1-methyl or 2-lower alkyl and $R_2$ is other than the group —$NR_4R_5$ may be prepared by alkylation of a compound of formula II

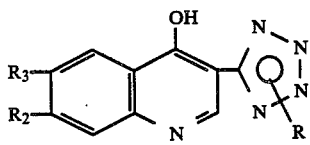

in which R is hydrogen, 1-methyl or 2-lower alkyl, $R_2$ is other than the group —$NR_4R_5$ and $R_3$ is as hereinbefore defined. The alkylation may be effected by reacting the compound of formula II with an alkylating agent, e.g. a dialkyl sulphate or an alkyl halide such as an alkyl iodide, in a conventional manner for such reactions. When R is hydrogen the reaction product is generally a mixture of a compound with an alkyl radical at the 1-position of the tetrazole ring and the corresponding compound with an alkyl radical at the 2-position of the tetrazole ring. Such a mixture of products may be separated in a conventional manner, for example by high pressure liquid chromatography.

The compounds of formula II may be prepared by reacting a compound of formula III,

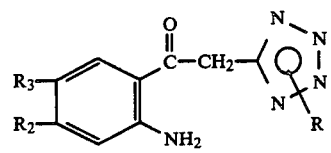

with a tri(lower alkyl)orthoformate, preferably trimethyl orthoformate or triethyl orthoformate.

The compounds of formula II in which R is hydrogen and $R_2$ is other than cyano may be prepared by reacting a compound of formula IV,

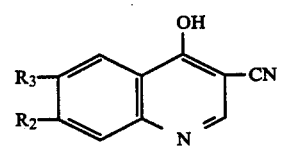

in which $R_2$ is other than cyano and $R_3$ is as hereinbefore defined, with sodium azide in the presence of ammonium chloride. This reaction is described in the specification of U.S. Pat. No. 4,035,368 and this specification discloses a number of substituted 4-hydroxyquinolines within formula II in which R is hydrogen.

The compounds of formula I in which the optional 2,3-bond is present may be prepared by reacting a compound of formula V,

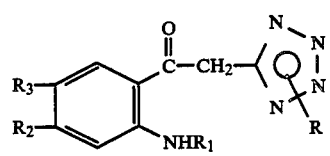

with a tri(lower alkyl)orthoformate, preferably trimethyl orthoformate or triethyl orthoformate.

The above-described ring-forming reactions with trialkyl orthoformate are effected by heating the reactants together in a suitable solvent. The reaction is catalysed by the presence of an acid, for example an organic carboxylic acid such as acetic acid or propionic acid, an organic base for example a secondary amine such as piperidine, or a mixture thereof.

The compounds of formula I in which the optional 2,3-bond is present may be prepared by reacting a compound of formula V with formic acid or the mixed anhydride of formic acid and acetic acid. These reactions may be effected at a temperature between 20° and 80°.

The intermediates of formulae III and V in which $R_2$ is other than cyano may be prepared by reacting a compound of formula VI,

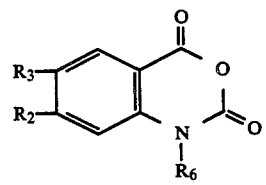

in which $R_2$ is other than cyano and $R_6$ is hydrogen or $R_1$, with an organometallic compound of formula VII,

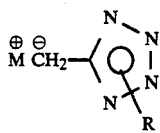 VII

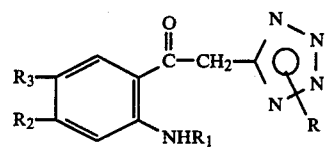 V in which M is an alkali metal, especially sodium or lithium and R is lower alkyl or the M atom. Reaction of the resulting compounds in which $R_2$ is fluoro with cyanide ion gives the intermediates of formula III and V in which $R_2$ is cyano.

The 1H-3,1-benzoxazine-2,4-diones of formula VI may be prepared by the method described in our United Kingom Patent No. 2,047,691.

The intermediates of formulae III and V in which $R_2$ is other than cyano may be prepared by reacting a compound of formula VII with a compound of formula VIII,

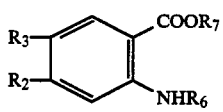 VIII in which $R_2$ is other than cyano and $R_7$ is lower alkyl, preferably methyl or ethyl.

The above-described intermediate of formulae II wherein R is 1-methyl or 2-lower alkyl, III and V are believed to be novel compounds.

The compounds of formula I which contain a 7-substituent selected from cyano, lower alkoxy and the amino group —$NR_4R_5$ may be prepared by reacting the corresponding 7-fluoro compounds with cyanide ion, lower alkoxide ion or the amine $HNR_4R_5$. Oxidation of the 7-amino group, for example with an organic percarboxylic acid, gives the N-oxide thereof.

The compounds of formula I which contain a 7-methylsulphinyl or 7-phenylsulphinyl substituent may also be prepared by oxidation of the corresponding 7-methylthio or 7-phenylthio compounds using, for example, an organic percarboxylic acid as the oxidising agent. These 7-alkylthio or 7-phenylthio compounds may be prepared by reacting the corresponding 7-fluoro compounds with the appropriate alkylsulphide or phenylsulphide ion.

The compounds of formula I which contain a 7-difluoromethoxy substituent may be prepared by reacting the corresponding 7-fluoro compound with hydroxide ion to give the corresponding 7-hydroxy compound, which is then reacted with chlorodifluoromethane to give the 7-difluoromethoxy compound.

The above-described reactions for preparing various 7-substituted compounds of formula I may be carried out using methods that are known in the art for analogous reactions. Thus, for example, in the reaction between a 7-fluoro compound of formula I and cyanide ion, the 7-fluoro compound and sodium cyanide may be heated in a suitable solvent, for example acetonitrile, preferably in the presence of a catalyst, for example a crown ether such as 18-crown-6.

The compounds of formula I in which the optional 2,3-bond is absent may be prepared by reacting a compound of formula V, with formaldehyde or a di(lower alkyl) acetal thereof. Examples of suitable reactants include paraformaldehyde and dimethoxymethane. The reaction may be effected in a suitable solvent and is preferably carried out in the presence of an acid catalyst, for example hydrogen chloride or an organic carboxylic acid, for example acetic acid.

The compounds of formula I in which the optional 2,3-bond in the quinolone ring is present may also be prepared by oxidation of the corresponding compounds in which the 2,3-bond is absent. This oxidation may be effected in a manner similar to that known for analogous reactions. Thus the oxidation may be carried out by bubbling air or oxygen through a solution or suspension of the 2,3-dihydro compound in a suitable liquid, preferably in the presence of a catalyst such as palladium/carbon. Basic conditions are preferred. Thus, for example, the reaction may be carried out in aqueous sodium hydroxide with a palladium/carbon catalyst at a temperature between 20° and 80°.

As mentioned above, the therapeutic activity of the quinolones of general formula I has been demonstrated by tests which include (A) the oral administration of the compounds to a strain of spontaneously hypertensive rat and (B) the intraduodenal administration of the compounds to a strain of normotensive rat. These tests were carried out in the following way:

Test A

Female rats weight range 180-240 g, of the Aoki-Okamoto strain of spontaneously hypertensive rat were used. The rats in groups of four were fasted overnight before administration of the test compound. Blood pressure was determined in the following way. The rats were placed in a cabinet kept at 38° C. with their tails protruding through holes in the cabinet. After 30 minutes in the cabinet blood pressure was measured using an inflatable cuff placed round the base of the tail and arterial pulsations monitored with a pneumatic pulse transducer. A pressure, greater than the expected blood pressure, was applied to the cuff, and this pressure was slowly reduced. The pressure in the cuff at which arterial pulsations reappeared was taken as the blood pressure. The rats were removed from the cabinet and each group orally dosed with a given dose of the test compound given as a solution or suspension in 0.25% aqueous carboxymethylcellulose. In addition to the pre-dosing reading, blood pressure was measured at 1.5 and 5.0 hours after dosing. A compound was designated as active if it gave a reduction of blood pressure of 20% or greater at either of these time intervals.

Test B

Male normotensive rats (Wistar strain) of weight range 210-240 g were used. The rats were anaesthetised and cannulae placed in a carotid artery and in the duodenum. Blood pressure was recorded electronically by means of a pressure transducer connected to the arterial cannula. The test compound was administered into the duodenum as a solution or suspension in 0.25% aqueous carboxymethylcellulose. Blood pressure was recorded before dosing and for 30 minutes afterwards. Results were obtained as the mean of determinations in three rats per dosage level. Compounds which caused an obvious drug-related fall in blood pressure of 14% or greater during the 30 minute post-dose period were designated as active.

The compounds of formula I identified in the following Examples were active in Test A at a dose of 90 mg/kg or less: Examples 1a, 2 to 23, 25, 27 to 34 and 36 to 40.

The compounds of formula I identified in the following Examples were not active in Test A at a dosage of 90 mg/kg but were active in Test B at a dose of 90 mg/kg: Examples 1b, 24, 26 and 35.

Compound which have activity in Test A at a dose of 90 mg/kg or less are preferred.

We have found that, in general, the compounds of formula I in which R is 1-methyl are more active in Test A than the corresponding compounds in which R is hydrogen or 2-lower alkyl.

The following compounds are particularly valuable compounds provided by the present invention.

1-methyl-3-(1-methyl-1H-tetrazol-5-yl)-4-quinolone
1,7-dimethyl-3-(1-methyl-1H-tetrazol-5-yl)-4-quinolone
7-ethyl-1-methyl-3-(1-methyl-1H-tetrazol-5-yl)-4-quinolone
7-chloro-1-methyl-3-(1-methyl-1H-tetrazol-5-yl)-4-quinolone
7-chloro-6-fluoro-3-(1-methyl-1H-tetrazol-5-yl)-4-quinolone The invention is illustrated by the following non-limitative Examples, in which parts and percentages are by weight and compositions of mixed solvents are given by volume. Novel compounds were characterised by one or more of the following spectroscopic techniques: nuclear magnetic resonance ($^1$H or $^{13}$C), infra red and mass spectroscopy. Temperatures are given in degrees Celsius.

EXAMPLE 1

A mixture of 4-hydroxy-3-(1H-tetrazol-5-yl)quinoline (0.76 g), potassium hydroxide (0.4 g), dimethyl sulphate (0.67 ml), tetrahydrofuran (20 ml) and water (50 ml) was stirred at room temperature for 1.5 hours. Dimethyl sulphate (0.67 ml) was added and stirring was continued for 1.5 hours. More dimethyl sulphate (0.67 ml) was added and stirring was continued for a further 1.5 hours, keeping the mixture basic throughout by the addition of 5N aqueous potassium hydroxide. The mixture was made strongly basic, kept overnight and then distilled to remove the tetrahydrofuran. The resulting aqueous solution was cooled and the resulting precipitate was crystallised from industrial methylated spirit to give two crops of product. A further crop of product was obtained by extracting the aqueous filtrate with dichloromethane. The three crops were combined and purified by high performance liquid chromatography over silica gel. Elution with ethyl acetate gave impure product A. Elution with ethyl acetate:isopropanol 9:1 gave product B.

(a) Product A was recrystallised from industrial methylated spirit to give the novel compound 1-methyl-3-(1-methyl-1H-tetrazol-5-yl)-4-quinolone, m.p. 220°-222°.

(b) Product B was recrystallised from industrial methylated spirit to give the novel compound 1-methyl-3-(2-methyl-2H-tetrazol-5-yl)-4-quinolone, m.p. 189°-192°.

EXAMPLE 2

(a) A stirred solution of 7-fluoro-1H-3,1-benzoxazine-2,4-dione (9.0 g) in dimethylacetamide (100 ml) at 18.5° was treated portionwise with sodium hydride (80% dispersion in mineral oil, 1.65) during 10 minutes. The mixture was stirred for a further 75 minutes. Methyl iodide (7.81 g) was then added dropwise to the stirred mixture during 5 minutes and the mixture was stirred for a further 18.5 hours at ambient temperature. Solvent (60 ml) was removed by distillation in vacuo. The residue was cooled to 3° and poured into ice-water. The resulting precipitate was collected, dried in vacuo and recrystallised from dichloromethane to give 7-fluoro-1-methyl-1H-3,1-benzoxazine-2,4-dione m.p. 158°-159.5°.

(b) A mixture of 7-fluoro-1-methyl-1H-3,1-benzoxazine-2,4-dione (20.0 g) and methanol (103 ml) was boiled under reflux. To the boiling mixture was added dropwise a solution of sodium methoxide (0.06 g) in methanol (50 ml.) during 19 minutes. The mixture was distilled in vacuo to remove solvent and give the product as a residue. There was thus obtained the novel compound methyl 4-fluoro-2-methylaminobenzoate as an oil which solidified on standing and was suitable for use in the next stage of synthesis. An analytical sample was prepared by distillation in vacuo followed by recrystallisation of the distillate from aqueous isopropanol. This sample had m.p. 39°-39.5°.

(c) A solution of butyl lithium in hexane (50 ml of 1.6M solution) was added slowly to a stirred mixture of 1,5-dimethyltetrazole (7.84 g) and dry tetrahydrofuran (170 ml) at 0°-5° under nitrogen. The mixture was stirred at 0°-5° for 0.5 hour and then methyl 4-fluoro-2-methylaminobenzoate (4.84 g) was added in portions at 0°-5°. The mixture was stirred at room temperature for 3 hours and then poured into water (500 ml). The resulting mixture was extracted with dichloromethane (5×60 ml). The extract was dried and evaporated to give an oil which partially solidified overnight. The solid was collected by filtration, washed with toluene and dried in vacuo to give the novel compound 1-(4-fluoro-2-methylaminophenyl)-2-(1-methyl-1H-tetrazol-5-yl)ethanone, m.p. 132°-134°.

(d) A mixture of the above ethanone (1.0 g), triethyl orthoformate (3.5 ml), toluene (17.5 ml), piperidine (4 drops) and propionic acid (2 drops) was boiled under reflux in a nitrogen atmosphere for 17 hours. The mixture was cooled and the solid product collected by filtration. The product was recrystallised from industrial methylated spirit using charcoal to give the novel compound 7-fluoro-1-methyl-3-(1-methyl-1H-tetrazol-5-yl)-4-quinolone, m.p. 264°-267°.

EXAMPLE 3

(a) Sodium (2.3 g) was dissolved in dry liquid ammonia (100 ml) containing a few crystals of ferric nitrate nonahydrate. 1,5-Dimethyltetrazole (9.8 g) was added and the mixture stirred for 1 hour. 1-Methyl-1H-3,1-benzoxazine-2,4-dione (8.85 g) was added and the mixture stirred for 2 hours. Ammonium chloride (5.45 g) was added cautiously, allowing the ammonia to evaporate. Water (200 ml) was added and the mixture allowed to stand overnight. The mixture was made weakly acid by the addition of acetic acid and extracted with dichloromethane (3×100 ml). The extract was dried over anhydrous magnesium sulphate and then evaporated.

The residue was triturated with toluene:ethyl acetate 1:1 to give, as a solid product, the novel compound 1-(2-methylaminophenyl)-2-(1-methyl-1H-tetrazol-5-yl)ethanone, m.p. 129°–130°.

(b) A mixture of the above ethanone (2.0 g), triethyl orthoformate (6.4 ml) and pyridine (25 ml) was boiled under reflux in a nitrogen atmosphere for 10 hours. More triethyl orthoformate (13 ml) was added and boiling under reflux was continued for a further 14 hours. The mixture was cooled and the crystalline product was collected, washed with ether and dried. Recrystallisation from industrial methylated spirit gave the novel compound 1-methyl-3-(1-methyl-1H-tetrazol-5-yl)-4-quinolone, m.p. 220°–222°, identical to the product of Example 1(a).

EXAMPLE 4

(a) A solution of butyl lithium in hexane (1.6M, 67.5 ml) was added to a stirred mixture of 5-methyltetrazole (4.54 g), and dry tetrahydrofuran (200 ml) at 0°. After stirring for 1 hour, 1-methyl-1H-3,1-benzoxazine-2,4-dione (9.6 g) was added and stirring continued for 65 hours at room temperature. The mixture was poured into water (300 ml) and acidified with 5N hydrochloric acid (12 ml). The organic phase was separated and the aqueous phase was extracted with dichloromethane (2×200 ml). The organic phases were combined, dried over anhydrous magnesium sulphate, and evaporated. The resulting solid was triturated with dichloromethane:industrial methylated spirit 9:1 (200 ml). The solid product was collected and recrystallised from ethyl acetate to give the novel compound 1-(2-methylaminophenyl)-2-(1H-tetrazol-5-yl)ethanone, m.p. 199°–201°.

(b) A mixture of the above ethanone (0.5 g), triethyl orthoformate (2.0 ml), propionic acid (1 drop), piperidine (2 drops) and toluene (10 ml.) was boiled under reflux for 4 hours. The mixture was cooled and the resulting solid product was collected by filtration, washed with diethyl ether and dried to give the novel compound 1-methyl-3-(1H-tetrazol-5-yl)-4-quinolone, m.p. 306°.

EXAMPLE 5

(a) A solution of butyl lithium in hexane (2.5M, 20 ml) was added slowly to a stirred solution of 1,5-dimethyltetrazole (4.9 g) in dry tetrahydrofuran (100 ml) at −5° to 0° under nitrogen. After stirring for 0.5 hour, 7-methyl-1H-3,1-benzoxazine-2,4-dione (2.6 g) was added and stirring continued for 1.5 hours at room temperature and for 3 hours at 40°. The solvent was evaporated under reduced pressure at 40°–50°, water (100 ml) was added to the residue, followed by 5N hydrochloric acid dropwise until neutral to Universal pH paper. The mixture was extracted with ethyl acetate (3×50 ml) and the combined extracts were washed with 10% aqueous potassium carbonate solution (50 ml), dried over anhydrous magnesium sulphate and then evaporated under reduced pressure at 50°. The residue was triturated with ether to give a solid product which was collected by filtration and recrystallised from ethyl acetate to give the novel compound 1-(2-amino-4-methylphenyl)-2-(1-methyl-1H-tetrazol-5-yl)ethanone, m.p. 155°–6°.

(b) A mixture of the above ethanone (1.7 g), triethyl orthoformate (30 ml) and acetic acid (2 ml) was boiled under reflux for 0.5 hour. The mixture was cooled and the resulting solid was collected by filtration. The solid was boiled with industrial methylated spirit (30 ml) and the novel compound 4-hydroxy-7-methyl-3-(1-methyl-1H-tetrazol-5-yl)quinoline, m.p. >320°, was separated by filtration from the hot (80°) mixture.

(c) Methyl iodide (0.38 ml) was added to a stirred mixture of the above 4-hydroxyquinoline (1.2 g), anhydrous potassium carbonate (0.68 g) and dry dimethylformamide (70 ml). The mixture was stirred at room temperature for 17 hours and the solvent removed by distillation under reduced pressure. Water (50 ml) was added to the residue and the mixture was extracted with dichloromethane (3×25 ml). The combined extracts were dried over anhydrous magnesium sulphate and evaporated to give a solid product which was crystallised from industrial methylated spirit to give the novel compound 1,7-dimethyl-3-(1-methyl-1H-tetrazol-5-yl)-4-quinolone, m.p. 254°–5°.

EXAMPLE 6

(a) A solution of phosgene (9.9 g) in toluene (100 ml) was added dropwise to a stirred solution of 2-amino-4-trifluoromethylbenzoic acid (6.9 g) and sodium carbonate (3.2 g) in water (100 ml) cooled in ice. Coolant was removed, the mixture was stirred for 2 hours, and the resulting solid was collected by filtration. The solid was dissolved in ethyl acetate and the solution was dried over anhydrous magnesium sulphate and then evaporated under reduced pressure. The resulting solid was crystallised from ethyl acetate to give the novel compound 7-trifluoromethyl-1H-3,1-benzoxazine-2,4-dione, m.p. 243°–245° (dec.)

(b) A solution of butyl lithium in hexane (2.7M, 11.1 ml) was added during 2 minutes to a stirred solution of 1,5-dimethyltetrazole (2.94 g) in dry tetrahydrofuran (100 ml) at −10° to −5°. After stirring for 15 minutes, 7-trifluoromethyl-1H-3,1-benzoxazine-2,4-dione (2.3 g) was added during 5 minutes at −10° to −5°. The reaction mixture was stirred at ambient temperature for 1 hour. Industrial methylated spirit (2 ml) was added and the mixture kept at ambient temperature for 1.5 hours. The mixture was evaporated to one quarter volume, then poured on to ice. The mixture was acidified to pH 2 with hydrochloric acid (5N). The solid product was collected, dried and recrystallised from ethyl acetate:diethyl ether to give the novel compound 1-(2-amino-4-trifluoromethylphenyl)-2-(1-methyl-1H-tetrazol-5-yl)ethanone, m.p. 200°–201°.

(c) A mixture of the above ethanone (0.8 g), triethyl orthoformate (5 ml) and acetic acid (1 drop) was stirred and boiled under reflux for 1 hour and then cooled to room temperature. The solid product was collected by filtration, washed with diethyl ether and dried to give the novel compound 4-hydroxy-3-(1-methyl-1H-tetrazol-5-yl)-7-trifluoromethylquinoline, m.p. 308°–310° (dec).

(d) A mixture of the above 4-hydroxyquinoline (0.79 g), anhydrous potassium carbonate (0.41 g), methyl iodide (0.18 ml) and dimethylformamide (20 ml) was stirred at room temperature for 15 hours. The mixture was filtered and the filtrate was evaporated under reduced pressure to give a residue. This residue was crystallised from industrial methylated spirit to give the novel compound 1-methyl-3-(1-methyl-1H-tetrazol-5-yl)-7-trifluoromethyl-4-quinolone, m.p. 220°–221°.

EXAMPLE 7

1-Methyl-3-(1-methyl-1H-tetrazol-5-yl)-4-quinolone (1.5 g) was dissolved in ethanol (600 ml). Hydrogen chloride gas was bubbled through the solution until saturation was achieved. The solvent was distilled off until 160 ml of the reaction solution remained. Diethyl ether (300 ml) was added and the solid product was collected and dried to give the novel compound 1-methyl-3-(1-methyl-1H-tetrazol-5-yl)-4-quinolone hydrochloride, m.p. 219°-221°.

EXAMPLE 8

(a) A solution of butyl lithium in hexane (1.6M, 20.8 ml) was added slowly to a stirred mixture of 1,5-dimethyltetrazole (3.26 g) and dry tetrahydrofuran (70 ml) at 0° under nitrogen. The mixture was stirred at 0° for 0.5 hour and then 7-chloro-1H-3,1-benzoxazine-2,4-dione (2.17 g) was added in portions at 0° to 5°. The mixture was stirred at room temperature for 3 hours, then poured into water (200 ml) and acidified with 5N hydrochloric acid to pH 6 to 7. The mixture was extracted with dichloromethane (4×70 ml). The extracts were combined, dried over anhydrous magnesium sulphate and evaporated to give the novel compound 1-(2-amino-4-chlorophenyl)-2-(1-methyl-1-H-tetrazol-5-yl)ethanone as an oil that was used in the next stage without purification.

(b) A mixture of the above ethanone, triethyl orthoformate (5 ml), propionic acid (2 drops), piperidine (4 drops) and toluene (70 ml) was boiled under reflux in a nitrogen atmosphere for 1 hour. The mixture was cooled and the solid product was collected by filtration, washed with toluene (3×5 ml) and dried to give the novel compound 7-chloro-4-hydroxy-3-(1-methyl-1H-tetrazol-5-yl)quinoline, m.p. 350°-351°.

(c) A mixture of the above 4-hydroxyquinoline (1.34 g), potassium hydroxide (0.34 g), dimethyl sulphate (0.6 ml) and water (60 ml) was stirred at room temperature for a total of 28 hours, adding more dimethyl sulphate after 5 hours (0.6 ml) and 17 hours (0.6 ml) and keeping the mixture basic throughout by the addition of 5N aqueous potassium hydroxide. The precipitate was collected by filtration, washed with water (2×20 ml), crystallised from industrial methylated spirit (70 ml) and dried to give the novel compound 7-chloro-1-methyl-3-(1-methyl-1H-tetrazol-5-yl)-4-quinolone, m.p. 270°-273°.

EXAMPLE 9

(a) A solution of butyl lithium in hexane (2.7M, 104 ml) was added slowly to a stirred solution of 1,5-dimethyltetrazole (27.5 g) in dry tetrahydrofuran (500 ml) at −5° to 0° under nitrogen. After stirring for 1.5 hours, 7-bromo-1H-3,1-benzoxazine-2,4-dione (22.6 g) was added and stirring continued for 18 hours at room temperature and for 3.5 hours at 40° to 50°. The mixture was cooled to room temperature, industrial methylated spirit (15 ml) added and most of the solvents distilled off. The residue was added to water (200 ml) and acidified with 5N hydrochloric acid to pH 1. The resulting solid was collected by filtration and crystallised from ethyl acetate to give the novel compound 1-(2-amino-4-bromophenyl)-2-(1-methyl-1H-tetrazol-5-yl)ethanone, m.p. 159°-160°.

(b) A mixture of the above ethanone (14.6 g), triethyl orthoformate (225 ml) and acetic acid (3 ml) was boiled under reflux for 2 hours. The mixture was cooled and the resulting solid was collected by filtration and washed with ether (100 ml) to give the novel compound 7-bromo-4-hydroxy-3-(1-methyl-1H-tetrazol-5-yl)quinoline, m.p. >300°.

(c) Methyl iodide (3.13 ml) was added to a stirred mixture of the above 4-hydroxyquinoline (14 g), anhydrous potassium carbonate (6.95 g) and dry dimethylformamide (400 ml). The mixture was stirred at room temperature for 3 hours and then filtered. The filtrate was evaporated and the residue crystallised from industrial methylated spirit to give the novel compound 7-bromo-1-methyl-3-(1-methyl-1H-tetrazol-5-yl)-4-quinolone, m.p. 292°-4°.

EXAMPLE 10

A mixture of sodium methoxide (0.47 g), 7-fluoro-1-methyl-3-(1-methyl-1H-tetrazol-5-yl)-4-quinolone (2.0 g) and methanol (40 ml) was boiled under reflux for 43 hours. The mixture was cooled and poured into water (100 ml). The solid was collected by filtration, washed with boiling industrial methylated spirit (50 ml) and dried to give the novel compound 7-methoxy-1-methyl-3-(1-methyl-1H-tetrazol-5-yl)-4-quinolone, m.p. 270°-273°.

EXAMPLE 11

(a) A solution of butyl lithium in hexane (2.7M, 9.8 ml) was added to a stirred solution of 1,5-dimethyltetrazole (2.6 g) in dry tetrahydrofuran (25 ml) at 0° under nitrogen. After 1 hour, 6,7-dimethyl-1H-3,1-benzoxazine-2,4-dione (1.69 g) was added and stirring was continued for 4 hours. The mixture was poured into water (200 ml), acidified with hydrochloric acid (5N) to pH 1, neutralised with aqueous sodium hydroxide (5N) and extracted with dichloromethane (3×100 ml). The combined extracts were dried and evaporated under reduced pressure. The residue was triturated with water to give a yellow solid which was collected by filtration and dried to give the novel compound 1-(2-amino-4,5-dimethylphenyl)-2-(1-methyl-1H-tetrazol-5-yl)ethanone, m.p. 162°-165°.

(b) A mixture of the above ethanone (1.45 g), triethyl orthoformate (20 ml) and acetic acid (0.7 ml) was boiled under reflux for 4.5 hours and then allowed to stand for 72 hours. The solid product was collected by filtration, washed with diethyl ether and dried to give the novel compound 4-hydroxy-6,7-dimethyl-3-(1-methyl-1H-tetrazol-5-yl)quinoline, m.p. 301°-303°.

(c) A mixture of the above 4-hydroxyquinoline (1.18 g), methyl iodide (0.55 ml), anhydrous potassium carbonate (0.68 g) and dimethylformamide (20 ml) was stirred at room temperature for 17 hours and then poured into water (80 ml). The precipitate was collected by filtration, dried and crystallised from methanol to give the novel compound 1,6,7-trimethyl-3-(1-methyl-1H-tetrazol-5-yl)-4-quinolone, m.p. 245°-246°.

EXAMPLE 12

(a) In a similar manner to that described in Example 8(a), 6-fluoro-1H-3,1-benzoxazine-2,4-dione was reacted with (1-methyl-1H-tetrazol-5-yl)methyl lithium to give the novel compound 1-(2-amino-5-fluorophenyl)-2-(1-methyl-1H-tetrazol-5-yl)ethanone. This product was isolated as a gum which was used in the next stage without further purification.

(b) A mixture of the above ethanone (16 g), triethyl orthoformate (100 ml) and acetic acid (1 ml) was boiled under reflux for 1.5 hours and then kept at room temperature overnight. The solid product was collected by filtration, washed with diethyl ether and crystallised from methanol:industrial methylated spirit to give the novel compound 6-fluoro-4-hydroxy-3-(1-methyl-1H-tetrazol-5-yl)quinoline, m.p. >300°.

(c) A mixture of the above 4-hydroxyquinoline (3.83 g), anhydrous potassium carbonate (2.15 g), dimethylformamide (50 ml) and methyl iodide (1 ml) was stirred at room temperature for 4 hours. The mixture was poured into water and acidified to pH 1 with 5N hydrochloric acid. The solid product was collected, washed with water (50 ml), dried and crystallised from industrial methylated spirit to give the novel compound 6-fluoro-1-methyl-3-(1-methyl-1H-tetrazol-5-yl)-4-quinolone, m.p. 260°–261°.

EXAMPLE 13

(a) In a similar manner to that described in Example 8a, 7-chloro-6-fluoro-1H-3,1-benzoxazine-2,4-dione (5.0 g, containing some of the corresponding 5-chloro-6-fluoro isomer) was reacted with (1-methyl-1H-tetrazol-5-yl)methyl lithium to give a mixture of the novel compound 1-(2-amino-4-chloro-5-fluorophenyl)-2-(1-methyl-1H-tetrazol-5-yl)ethanone and the novel compound 1-(2-amino-6-chloro-5-fluorophenyl)-2-(1-methyl-1H-tetrazol-5-yl)ethanone. This mixture was separated by flash chromatography [described in J. Org. Chem., 43, 2923-5 (1978)] over a silica gel sold under the trade name Kieselgel 60 using dichloromethane:industrial methylated spirit 95:5 as the eluent to give 1-(2-amino-4-chloro-5-fluorophenyl)-2-(1-methyl-1H-tetrazol-5-yl)ethanone, m.p. 180°–184°.

(b) A mixture of the above ethanone (3.8 g), acetic acid (1.6 ml) and triethyl orthoformate (40 ml) was boiled under reflux for 5.5 hours and then kept at room temperature for 72 hours. The solid product was collected by filtration, washed with diethyl ether and dried to give the novel compound 7-chloro-6-fluoro-4-hydroxy-3-(1-methyl-1H-tetrazol-5-yl)quinoline, m.p. 326°–330°.

(c) A mixture of the above 4-hydroxyquinoline (3.7 g), anhydrous potassium carbonate (1.92 g), methyl iodide (1.5 ml) and dimethylformamide (50 ml) was stirred at room temperature for 1.5 hours and then poured into water. The solid product was collected by filtration, dried and crystallised from methanol to give the novel compound 7-chloro-6-fluoro-1-methyl-3-(1-methyl-1H-tetrazol-5-yl)-4-quinolone, m.p. 264°–267°.

EXAMPLE 14

(a) Chromium trioxide (4.7 g) was added in small portions to a stirred suspension of 6-chloro-5-methoxyisatin (5.9 g) in glacial acetic acid (22 ml) and acetic anhydride (22 ml) at 80°. Some spontaneous ignition of the chromium trioxide was observed where this reagent became exposed to the air in the stirring vortex. The mixture was cooled and diluted with water (100 ml). The solid product was recrystallised from industrial methylated spirit to give the novel compound 7-chloro-6-methoxy-1H-3,1-benzoxazine-2,4-dione containing some unreacted starting material.

(b) In a similar manner to that described in Example 8a, the above benzoxazine was reacted with (1-methyl-1H-tetrazol-5-yl)-methyl lithium to give the novel compound 1-(2-amino-4-chloro-5-methoxyphenyl)-2-(1-methyl-1H-tetrazol-5-yl)ethanone, m.p. 178°–181°.

(c) A mixture of the above ethanone (1.09 g), acetic acid (0.5 ml) and triethyl orthoformate (13 ml) was boiled under reflux for 4 hours, then cooled to room temperature. The solid product was collected by filtration, washed with diethyl ether and dried to give the novel compound 7-chloro-4-hydroxy-6-methoxy-3-(1-methyl-1H-tetrazol-5-yl)quinoline, m.p. 317°–320° (dec).

(d) A mixture of the above 4-hydroxyquinoline (0.95 g), anhydrous potassium carbonate (0.47 g), methyl iodide (0.37 ml) and dimethylformamide (13 ml) was stirred at room temperature for 18 hours. The solvent was evaporated under reduced pressure and the residue was triturated with water (50 ml). The resulting solid product was collected by filtration and crystallised from industrial methylated spirit to give the novel compound 7-chloro-6-methoxy-1-methyl-3-(1-methyl-1H-tetrazol-5-yl)-4-quinolone, m.p. 305°–310° (dec).

EXAMPLE 15

(a) A solution of benzenethiol (2.3 ml) and sodium hydroxide (0.9 g) in industrial methylated spirit (50 ml) was added to a stirred suspension of 7-fluoro-1-methyl-3-(1-methyl-1H-tetrazol-5-yl)-4-quinolone at room temperature. The mixture was stirred and boiled under reflux for 76 hours, concentrated to one-half volume, and poured into water (200 ml). The precipitate was collected by filtration, dried and crystallised from industrial methylated spirit. The resulting product was purified by flash chromatography over a column of Kieselgel 60 using dichoromethane:industrial methylated spirit 9:1 as the eluent. Crystallization from industrial methylated spirit gave the novel compound 1-methyl-3-(1-methyl-1H-tetrazol-5-yl)-7-phenylthio-4-quinolone, m.p. 190°–193°.

(b) A solution of 3-chloroperbenzoic acid (85%, 0.81 ml) in dichloromethane (25 ml) was added dropwise during 10 minutes to a solution of the above quinolone (1.4 g) in dichloromethane (70 ml) at −10°. The mixture was stirred at −10° for 1 hour and then stirred vigorously with saturated aqueous sodium bicarbonate solution (100 ml). The aqueous layer was separated and extracted with dichloromethane (2×40 ml). The combined organic phases were dried over anhydrous magnesium sulphate and evaporated. The solid residue was crystallised from industrial methylated spirit to give the novel compound 1-methyl-3-(1-methyl-1H-tetrazol-5-yl)-7-phenylsulphinyl-4-quinolone, m.p. 217°–220°.

EXAMPLE 16

A mixture of 1-methyl-3-(1H-tetrazol-5-yl)-4-quinolone (0.74 g), isopropyl bromide (0.31 ml), anhydrous potassium carbonate (0.45 g) and butanone (30 ml) was boiled under reflux for 16 hours. More isopropyl bromide (0.5 ml) was added and boiling under reflux was continued for 7 hours. More isopropyl bromide (0.5 ml) was added and boiling under reflux was continued for a further 24 hours. The mixture was evaporated to dryness and the residue treated with water (30 ml). The solid product was collected by filtration and partially purified by high pressure liquid chromatography over silica gel using dichloromethane:methanol 95:5 as the eluent. The solid product was recrystallised from ethyl acetate:diethyl ether 3:2 to give the novel compound 3-(2-isopropyl-1H-tetrazol-5-yl)-1-methyl-4-quinolone, m.p. 134°–137°.

EXAMPLE 17

A mixture of 1-(4-fluoro-2-methylaminophenyl)-2-(1-methyl-1H-tetrazol-5-yl)ethanone (2.0 g), dimethoxymethane (40 ml) and ethanolic hydrogen chloride (4 ml) was boiled under reflux for 1.5 hours and then evaporated under reduced pressure. The residue was triturated with diethyl ether and collected by filtration. The resulting solid was boiled with tetrahydrofuran:water 3:7 (5 ml). The mixture was allowed to cool and the solid was collected and recrystallised from methanol to give the novel compound 7-fluoro-1-methyl-3-(1-methyl-1H-tetrazol-5-yl)-1H-2,3-dihydro-4-quinolinone, m.p. 178°–179°.

EXAMPLE 18

A mixture of 1-(2-methylaminophenyl)-2-(1-methyl-1H-tetrazol-5-yl)ethanone (2.0 g), dimethoxymethane (20 ml), dichloromethane (20 ml) and ethanolic hydrogen chloride (10 ml) was stirred at room temperature for 1 hour and then evaporated under reduced pressure. The solid residue was crystallised from methanol:diethyl ether 4:1 to give the novel compound 1-methyl-3-(1-methyl-1H-tetrazol-5-yl)-1H-2,3-dihydro-4-quinolinone, m.p. 170°–171°.

EXAMPLE 19

(a) A solution of butyl lithium in hexane (2.7M, 53 ml) was added to a stirred suspension of 5-methyltetrazole (6.0 g) in dry tetrahydrofuran (250 ml) at 0° under nitrogen. A solution of methyl 4-fluoro-2-methylaminobenzoate (4.36 g) in dry tetrahydrofuran (20 ml) was added during 10 minutes. The mixture was stirred for 17 hours at room temperature and then for 3 hours at 40° to 70°. The mixture was cooled to room temperature and water (200 ml) was added. The mixture was neutralised with dilute aqueous hydrochloric acid and extracted with dichloromethane (3×100 ml). The combined extracts were dried and evaporated under reduced pressure. The residue was crystallised from industrial methylated spirit to give the novel compound 1-(4-fluoro-2-methylaminophenyl)-2-(1H-tetrazol-5-yl)ethanone, m.p. 214°–6°.

(b) A mixture of the above ethanone (0.7 g), triethyl orthoformate (10 ml) and acetic acid (0.1 ml) was boiled under reflux for 2 hours and then cooled to room temperature. The precipitate was collected by filtration and crystallised from industrial methylated spirit to give the novel compound 7-fluoro-1-methyl-3-(1H-tetrazol-5-yl)-4-quinolone 0.85 hydrate m.p. 290°–292°.

EXAMPLE 20

(a) In a similar way to that described in Example 8a, 1H-3,1-benzoxazine-2,4-dione was reacted with (1-methyl-1H-tetrazol-5-yl)methyl lithium to give the novel compound 1-(2-aminophenyl)-2-(1-methyl-1H-tetrazol-5-yl)ethanone, m.p. 128°–132° (from ethyl acetate).

(b) In a similar way to that described in Example 11b, the above ethanone was reacted with triethyl orthoformate to give the novel compound 4-hydroxy-3-(1-methyl-1H-tetrazol-5-yl)quinoline, m.p. 318°–320°.

(c) A mixture of the above hydroxyquinoline (2 g), anhydrous potassium carbonate (1.83 g), butyl bromide (1.0 ml) and dimethylformamide (100 ml) was stirred and heated on the steam bath for 34 hours. More butyl bromide (0.1 ml) was added and heating continued for 3 hours. The mixture was kept for 70 hours, and then evaporated under reduced pressure. The residue was heated with industrial methylated spirit (150 ml) and filtered. Diethyl ether (150 ml) was added to the filtrate, causing a white solid to precipitate. The mixture was filtered and the filtrate evaporated under reduced pressure. The residue was crystallised from ethyl acetate, washed with diethyl ether and dried to give the novel compound 1-butyl-3-(1-methyl-1H-tetrazol-5-yl)-4-quinolone, m.p. 100°–105°.

EXAMPLE 21

A mixture of 4-hydroxy-3-(1-methyl-1H-tetrazol-5-yl)quinoline (2 g), ethyl iodide (1.1 ml), anhydrous potassium carbonate (1.83 g) and dimethylformamide (100 ml) was stirred and heated on a steam bath for 18 hours. The mixture was evaporated under reduced pressure and the residue dissolved in industrial methylated spirit (100 ml). Dilution with diethyl ether (100 ml) gave a white precipitate which was collected and extracted with hot dichloromethane (100 ml). The extract was evaporated to give the novel compound 1-ethyl-3-(1-methyl-1H-tetrazol-5-yl)-4-quinolone, m.p. 170°–176°.

EXAMPLE 22

(a) A solution of phosgene (45 g) in toluene (160 ml) was added during 20 minutes to a stirred solution of 2-amino-4,5-difluorobenzoic acid (26 g) in aqueous sodium carbonate (20.7 g anhydrous sodium carbonate in 350 ml water), keeping the temperature below 40°. The mixture was stirred at room temperature for 15 hours. The solid product was collected by filtration, washed with water and dried to give the novel compound 6,7-difluoro-1H-3,1-benzoxazine-2,4-dione, m.p. 223°–226° (dec.).

(b) In a similar manner to that described in Example 8(a), the above benzoxazine (8.7 g) was reacted with (1-methyl-1H-tetrazol-5-yl)methyl lithium to give the novel compound 1-(2-amino-4,5-difluorophenyl)-2-(1-methyl-1H-tetrazol-5-yl)ethanone, m.p. 162°–164° (from ethyl acetate).

(c) A mixture of the above ethanone (4 g), triethyl orthoformate (75 ml) and glacial acetic acid (2 ml) was boiled under reflux for 30 minutes. The mixture was cooled to room temperature and diluted with diethyl ether. The precipitate was collected, washed with diethyl ether and dried to give the novel compound 6,7-difluoro-4-hydroxy-3-(1-methyl-1H-tetrazol-5-yl)quinoline m.p. >300°.

(d) A mixture of the above 4-hydroxyquinoline (4.1 g), dimethylformamide (200 ml), anhydrous potassium carbonate (2 g) and methyl iodide (2.28 g) was stirred at room temperature for 3 hours and then left at room temperature for 63 hours. Ammonia solution (0.88, 2 ml) was added and the mixture was evaporated to dryness. The residue was treated with water (100 ml). The solid product was collected and purified by trituration with boiling ethyl acetate to give the novel compound 6,7-difluoro-1-methyl-3-(1-methyl-1H-tetrazol-5-yl)-4-quinolone, m.p. 253°–225°.

EXAMPLE 23

(a) A solution of butyl lithium in hexane (2.7M, 13.4 ml) was added to a solution of 1,5-dimethyltetrazole (3.54 g) in dry tetrahydrofuran (83 ml) at 0° under nitrogen. The mixture was stirred for 0.5 hour and 7-ethyl-1H-3,1-benzoxazine-2,4-dione (2.3 g) was added. The mixture was allowed to warm to room temperature during 2 hours. Water (100 ml) was added. The mixture was acidified to pH 1 with hydrochloric acid (5N) and then neutralised with aqueous sodium hydroxide (5N). The mixture was extracted with dichloromethane (2×100 ml). The extract was dried and evaporated. The residue was purified by flash chromatography on Kieselgel 60 using dichloromethane:industrial methylated spirit 99:1 as the eluent. This gave the novel compound 1-(2-amino-4-ethylphenyl)-2-(1-methyl-1H-tetrazol-5-yl)ethanone in crude form as an oil.

(b) A mixture of the above ethanone (1.95 g), triethyl orthoformate (27 ml) and glacial acetic acid (1 ml) was boiled under reflux for 3 hours. The mixture was cooled to room temperature. The precipitate was collected by filtration, washed with diethyl ether and dried to give the novel compound 7-ethyl-4-hydroxy-3-(1-methyl-1H-tetrazol-5-yl)quinoline, m.p. 270°–273°.

(c) A mixture of the above 4-hydroxyquinoline (1.45 g), anhydrous potassium carbonate (0.82 g), methyl iodide (0.65 ml) and dimethyl formamide (22 ml) was stirred at room temperature for 17 hours. The solvent was evaporated under reduced pressure and the residue was triturated with water. The resultant solid product was collected, dried and crystallized from ethyl acetate to give the novel compound 7-ethyl-1-methyl-3-(1H-tetrazol-5-yl)-4-quinolone, m.p. 180°–181°.

EXAMPLE 24

(a) A mixture of 6-methyl-1H-3,1-benzoxazine-2,4-dione (2 g), anhydrous potassium carbonate (0.64 g), dimethylformamide (10 ml) and methyl iodide (0.9 ml) was stirred at room temperature for 24 hours. More methyl iodide (0.9 ml) was added and stirring continued for a further 18 hours. More potassium carbonate (1 g) and methyl iodide (0.8 ml) were added and stirring continued for a further 23 hours. The mixture was poured on to a mixture of ice and water. The resulting precipitate was washed with water and dried to give the novel compound 1,6-dimethyl-1H-3,1-benzoxazine-2,4-dione, m.p. 165°–170°.

(b) In a similar manner to that described in Example 8(a), the above benzoxazine (5.7 g) was reacted with (1-methyl-1H-tetrazol-5-yl)methyl lithium to give the novel compound 1-(5-methyl-2-methylaminophenyl)-2-(1-methyl-1H-tetrazol-5-yl)ethanone, m.p. 141°–143° (from ethyl acetate).

(c) Glacial acetic acid (0.5 ml) was added to a solution of the above ethanone (3 g) in triethyl orthoformate (60 ml). The mixture was boiled under reflux for 4.5 hours and kept at room temperature overnight. The solid product was collected by filtration, washed with diethyl ether and dried to give the novel compound 1,6-dimethyl-3-(1-methyl-1H-tetrazol-5-yl)-4-quinolone, m.p. 281°–282°.

EXAMPLE 25

A mixture of 7-fluoro-1-methyl-3-(1-methyl-1H-tetrazol-5-yl)-4-quinolone (5.0 g), aqueous sodium hydroxide (5N, 80 ml) and industrial methylated spirit (10 ml) was boiled under reflux for 160 hours. Reaction was incomplete. The hot reaction mixture was filtered and the residue extracted with hot dimethylformamide (40 ml). The extract was evaporated to give a crude product. A mixture of this crude product and ethanolic sodium ethoxide (0.13 g sodium in 110 ml absolute ethanol) was boiled under reflux for 50 hours. The hot reaction mixture was filtered and the filtrate cooled in ice. The precipitate was collected and purified by flash chromatography on Kieselgel 60 using dichloromethane:industrial methylated spirit 9:1 as the eluent. The purified product was recrystallised from industrial methylated spirit to give the novel compound 7-ethoxy-1-methyl-3-(1-methyl-1H-tetrazol-5-yl)-4-quinolone, m.p. 214°–217°.

EXAMPLES 26

7-Fluoro-1-methyl-3-(1-methyl-1H-tetrazol-5-yl)-4-quinolone (5 g) was added to a solution of sodium (0.9 g) in butanol (50 ml) and the mixture was heated at 100° for 19 hours. The mixture was poured into water (200 ml). The resulting precipitate was collected and recrystallised twice from industrial methylated spirit to give the novel compound 7-butoxy-1-methyl-3-(1-methyl-1H-tetrazol-5-yl)-4-quinolone, m.p. 187°–190°.

EXAMPLE 27

A mixture of 7-fluoro-1-methyl-3-(1-methyl-1H-tetrazol-5-yl)-4-quinolone (5.25 g), sodium cyanide (1.0 g), crown ether (18-crown-6, 5.4 g) and acetonitrile (200 ml) was stirred and boiled under reflux for 79 hours, left at ambient temperature for 70 hours, and boiled under reflux for 24 hours. The mixture was cooled and filtered. The residue was boiled with industrial methylated spirit (200 ml) and the mixture filtered while hot. The residue was further extracted twice with boiling 50% aqueous industrial methylated spirit (400 ml, then 200 ml). Each hot extract precipitated a solid when cooled. The three solids were combined and recrystallised from 50% aqueous industrial methylated spirit to give a crude product. This product was purified by high pressure liquid chromatography on silica, using dichloromethane:methanol 9:1 as the eluent. The eluent was evaporated to give a residue which was recrystallised from 30% aqueous industrial methylated spirit to give the novel compound 7-cyano-1-methyl-3-(1-methyl-1H-tetrazol-5-yl)-4-quinolone, m.p. 301°–303°.

EXAMPLE 28

(a) A mixture of 7-fluoro-1-methyl-3-(1-methyl-1H-tetrazol-5-yl)-4-quinolone (5 g) and aqueous sodium hydroxide (5N, 80 ml) was stirred and boiled under reflux for 45 hours. Water (180 ml) was added to the mixture which was then cooled to ambient temperature. The solution was acidified with concentrated hydrochloric acid to pH 4. The resulting precipitate was collected by filtration and washed with boiling industrial methylated spirit (300 ml) and then hot butanol (120 ml). The residue was crystallised from 50% aqueous industrial methylated spirit to give the novel compound 7-hydroxy-1-methyl-3-(1-methyl-1H-tetrazol-5-yl)-4-quinolone, m.p. >320°.

(b) Chlorodifluoromethane was bubbled through a stirred solution of the above quinolone (2.25 g) and sodium hydroxide (1.75 g) in 40% aqueous dioxan (25 ml) at 90° for 1 hour. Dioxan (10 ml) and water (5 ml) were added and passage of chlorodifluoromethane was continued for 1 hour. Dioxan (10 ml) was added and passage of chlorodifluoromethane was continued for a further 4 hours. The mixture was kept at ambient temperature overnight. The solid product was collected by filtration and recrystallised from industrial methylated spirit to give the novel compound 7-difluoromethoxy-1-methyl-3-(1-methyl-1H-tetrazol-5-yl)-4-quinolone, m.p. 225°–228°.

EXAMPLE 29

(a) A solution of butyl lithium in hexane (2.5M, 18.5 ml) was added to a stirred solution of 1,5-dimethyl-tetrazole (4.55 g) in dry tetrahydrofuran (100 ml) at 0°. After 30 minutes methyl 2-amino-5-methoxybenzoate (2.8 g) was added and stirring was continued for 3 hours. The reaction mixture was poured into water (200 ml), acidified with hydrochloric acid (5N) to pH 1, and extracted with dichloromethane (3×100 ml). The extract was dried over anhydrous magnesium sulphate and evaporated. The residue was recrystallised from industrial methylated spirit to give the novel compound 1-(2-amino-5-methoxyphenyl)-2-(1-methyl-1H-tetrazol-5-yl)ethanone, m.p. 170°–172°.

(b) A mixture of the above ethanone (5.2 g), triethyl orthoformate (19.4 ml), piperidine (24 drops), propionic acid (12 drops) and toluene (25 ml) was boiled under reflux for 5 hours. The mixture was cooled. The solid product was collected, washed with diethyl ether and dried to give the novel compound 4-hydroxy-6-methoxy-3-(1-methyl-1H-tetrazol-5-yl)quinoline.

(c) A mixture of the above 4-hydroxyquinoline (2.57 g), anhydrous potassium carbonate (1.45 g), methyl iodide (1.1 ml) and dimethylformamide (38 ml) was stirred for 1 hour. The solvent was evaporated under reduced pressure. The residue was treated with water and extracted with dichloromethane (3×50 ml). The extract was dried over anhydrous magnesium sulphate and evaporated under reduced pressure. The residue was crystallised from industrial methylated spirit to give the novel compound 6-methoxy-1-methyl-3-(1-methyl-1H-tetrazol-5-yl)-4-quinolone, m.p. 280°–283°.

EXAMPLE 30

A mixture of 7-fluoro-1-methyl-3-(1-methyl-1H-tetrazol-5-yl)-4-quinolone (0.2 g) and piperidine (5 ml) was heated on a steam bath for 22 hours. The mixture was cooled and the solid product was collected and recrystallised from industrial methylated spirit to give the novel compound 1-methyl-3-(1-methyl-1H-tetrazol-5-yl)-7-piperidino-4-quinolone, m.p. 180°–183°.

EXAMPLE 31

Saturated ethanolic hydrogen chloride (30 ml) was added to a suspension of the 4-quinolone of Example 30 (1.0 g) in absolute ethanol (10 ml). The resulting solution was kept at ambient temperature for 24 hours, then evaporated under reduced pressure and the residue was crystallised from ethyl acetate:industrial methylated spirit 4:1 to give the hydrochloride salt of 1-methyl-3-(1-methyl-1H-tetrazol-5-yl)-7-piperidino-4-quinolone solvated with 0.5 mole ethyl acetate, m.p. 173°–176°.

EXAMPLE 32

To a stirred solution of the 4-quinolone of Example 30 (1.44 g) in dichloromethane (100 ml) was added a solution of 3-chloroperbenzoic acid (85%, 0.86 g) in dichloromethane (20 ml) and the mixture was stirred for 52 hours. A solution of 3-chloroperbenzoic acid (85%, 0.27 g) in dichloromethane (10 ml) was added and the mixture was stirred for 20 hours. Saturated aqueous sodium bicarbonate (40 ml) was added and the mixture was stirred for 45 minutes. The mixture was evaporated to dryness and the residue was extracted with dichloromethane (75 ml) for 1.5 hours using a Soxhlet apparatus. The extract was evaporated and the residue was crystallised from industrial methylated spirit:diethyl ether 4:1 to give 1-[1-methyl-3-(1-methyl-1H-tetrazol-5-yl)-4-oxo-1,4-dihydroquinolin-7-yl]piperidine 1-oxide monohydrate, m.p. 163°–166°.

EXAMPLE 33

In a similar way to that described in Example 30, 7-fluoro-1-methyl-3-(1-methyl-1H-tetrazol-5-yl)-4-quinolone (5 g) was boiled under reflux with pyrrolidine (50 ml) for 20 hours to give 1-methyl-3-(1-methyl-1H-tetrazol-5-yl)-7-pyrrolidino-4-quinolone, m.p. 267°–270° (from industrial methylated spirit:water 5:1).

EXAMPLE 34

In a similar way to that described in Example 30, 7-fluoro-1-methyl-3-(1-methyl-1H-tetrazol-5-yl)-4-quinolone (1 g) was heated with morpholine (25 ml) at 100° for 103 hours to give 1-methyl-3-(1-methyl-1H-tetrazol-5-yl)-7-morpholino-4-quinolone, m.p. 235°–238°.

EXAMPLE 35

(a) Methanethiol was bubbled through an ice-cooled solution of sodium hydroxide (3.2 g) in water (200 ml) until the solution was saturated. 7-Fluoro-1-methyl-3-(1-methyl-1H-tetrazol-5-yl)-4-quinolone (10 g) was added. The mixture was stirred at ambient temperature for 5 hours and then at 100° for 27 hours. The cooled mixture was filtered and the solid product was collected, washed with water and then with boiling industrial methylated spirit to give the novel compound 1-methyl-3-(1-methyl-1H-tetrazol-5-yl)-7-methylthio-4-quinolone, m.p. 277°–280°.

(b) To a stirred suspension of the above 4-quinolone (2.5 g) in dichloromethane (150 ml) at 0° was added a solution of 3-chloroperbenzoic acid (85%, 1.2 g) in dichloromethane (30 ml) dropwise during 15 minutes. The mixture was stirred at 0° for 55 minutes. More 3-chloroperbenzoic acid (85%, 0.15 g) was added and stirring at 0° continued for 1 hour. Saturated aqueous sodium bicarbonate solution (150 ml) was added and the mixture was stirred vigorously at ambient temperature for 30 minutes, and then filtered. The organic phase of the filtrate was separated and the aqueous phase was extracted with dichloromethane (2×30 ml). The organic phases were combined, dried and evaporated. The residue was purified by flash chromatography on Kieselgel 60 using dichloromethane:industrial methylated spirit 9:1 as the eluent. There was obtained the novel compound 1-methyl-7-methylsulphinyl-3-(1-methyl-1H-tetrazol-5-yl)-4-quinolone, m.p. 237°–240°.

EXAMPLE 36

A mixture of 1-(2-methylaminophenyl)-2-(1-methyl-1H-tetrazol-5-yl)ethanone (2 g), paraformaldehyde (0.26 g) and glacial acetic acid (40 ml) was stirred and boiled under reflux for 45 minutes. The acetic acid was evaporated under reduced pressure and the solid residue was dissolved in dichloromethane (100 ml). The solution was washed with water, dried over anhydrous magnesium sulphate and evaporated. The residue was crystallised from industrial methylated spirit to give the novel compound 1-methyl-3-(1-methyl-1H-tetrazol-5-yl)-1H-2,3-dihydro-4-quinolinone, m.p. 169°–171°, identical to the product of Example 18.

EXAMPLE 37

Air was bubbled through a mixture of 1-methyl-3-(1-methyl-1H-tetrazol-5-yl)-1H-2,3-dihydro-4-quinolinone (0.2 g), palladium on carbon (10%, 0.03 g) aqueous sodium hydroxide (5N, 10 ml) and water (20 ml) for 3.25 hours at ambient temperature. The mixture was diluted with water (20 ml) and extracted with dichloromethane (3×30 ml). The extract was dried over anhydrous magnesium sulphate and evaporated. The solid residue was crystallised from industrial methylated spirit to give the novel compound 1-methyl-3-(1-methyl-1H-tetrazol-5-yl)-4-quinolone, m.p. 219°-222°, identical to the product of Example 1(a).

EXAMPLE 38

A mixture of 1-(2-methylaminophenyl)-2-(1-methyl-1H-tetrazol-5-yl)ethanone (0.2 g) and formic acid (5 ml) was heated on a steam bath for 16 hours. The mixture was cooled to ambient temperature and diluted with diethyl ether (80 ml). The resulting precipitate was collected and crystallised from industrial methylated spirit to give the novel compound 1-methyl-3-(1-methyl-1H-tetrazol-5-yl)-4-quinolone, m.p. 219°-221°, identical to the product of Example 1(a).

EXAMPLE 29

A mixture of 7-fluoro-1-methyl-3-(1-methyl-1H-tetrazol-5-yl)-4-quinolone (10 g), thiomorpholine (10 g) and dimethylformamide (20 ml) was heated at 100° for 22 hours and then at 140° for 5.5 hours. The mixture was cooled and poured into water (220 ml). The resulting precipitate was collected and purified by high performance liquid chromatography on silica using dichloromethane:industrial methylated spirit:isopropanol 98.25:0.5:1.25 as the eluent. This gave the novel compound 7-dimethylamino-1-methyl-3-(1-methyl-1H-tetrazol-5-yl)-4-quinolone, m.p. 280°-283°.

EXAMPLE 40

A mixture of acetic anhydride (0.8 ml) and formic acid (0.4 ml) was stirred at 50°-60° for 2 hours, then cooled to ambient temperature. 1-(4-Fluoro-2-methylaminophenyl)-2-(1-methyl-1H-tetrazol-5-yl)ethanone (1.03 g) was added. The mixture was stirred at ambient temperature for 5 hours, then kept at this temperature for 16 hours. The mixture was triturated under light petroleum to give a solid product. This product was extracted with boiling ethyl acetate (100 ml) and the extract cooled to give a solid product which was recrystallised from industrial methylated spirit to give the novel compound 7-fluoro-1-methyl-3-(1-methyl-1H-tetrazol-5-yl)-4-quinolone, m.p. 264°-267°, identical to the product of Example 2(d).

EXAMPLE 41

In the preparation of capsules, 100 parts by weight of active compound and 250 parts by weight of lactose are de-aggregated and blended. The mixture is filled into hard gelatin capsules, each capsule containing 100 mg of active compound.

EXAMPLE 42

Tablets are prepared from the following ingredients.

|  | parts by weight |
|---|---|
| Active compound | 100 |
| Lactose | 100 |
| Maize starch | 22 |
| Polyvinylpyrrolidone | 10 |
| Magnesium stearate | 3 |

The active compound, the lactose and some of the starch are de-aggregated, blended and the resulting mixture is granulated with a solution of the polyvinylpyrrolidone in ethanol. The dry granulate is blended with the magnesium stearate and the rest of the starch. The mixture is then compressed in a tableting machine to give tablets containing 100 mg active compound.

EXAMPLE 43

Tablets are prepared by the method of Example 42. The tablets are enteric coated in a conventional manner using a solution of 20% cellulose acetate phthalate and 3% diethyl phthalate in ethanol:dichloromethane 1:1.

EXAMPLE 44

In the preparation of suppositories, 100 parts by weight of active compound is incorporated in 1300 parts by weight of tri-glyceride suppository base and the mixture formed into suppositories each containing 100 mg of active compound.

We claim:

1. A quinolone of the formula I

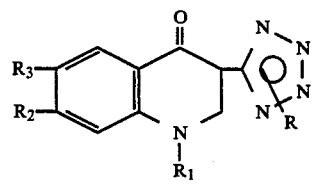

in which the dotted lines between positions 2 and 3 of the quinolone ring represents an optional bond, R is hydrogen, 1-methyl or 2-lower alkyl; $R_1$ is lower alkyl; $R_2$ is hydrogen, halo, lower alkyl, lower alkoxy, trifluoromethyl, cyano, difluoromethoxy, methylsulphinyl, phenylsulphinyl or the group —$NR_4R_5$ or the N-oxide thereof wherein $R_4$ and $R_5$ are the same or different lower alkyl; and $R_3$ is hydrogen, fluoro, lower alkyl or lower alkoxy provided that, when $R_3$ is lower alkoxy, $R_2$ is other than lower alkoxy.

2. A quinolone according to claim 1 in which R is hydrogen.

3. A quinolone according to claim 1 in which R is 1-methyl.

4. A quinolone according to claim 1 of formula IX

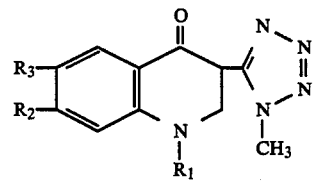

in which $R_1$ is lower alkyl, $R_2$ is hydrogen, halo, lower alkyl, lower alkoxy, trifluoromethyl, cyano or difluoromethoxy and $R_3$ is hydrogen, fluoro, lower alkyl or lower alkoxy, provided that when $R_3$ is lower alkoxy, $R_2$ is other than lower alkoxy.

5. A quinolone according to claim 4 in which the lower alkyl and lower alkoxy moieties are of one carbon atom.

6. A quinolone according to claim 5 in which $R_3$ is fluoro.

7. A quinolone according to claim 5 in which $R_3$ is hydrogen.

8. A quinolone according to claim 1 of formula X

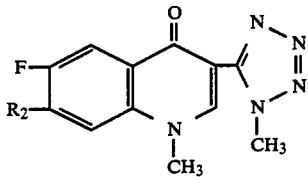

in which $R_2$ is hydrogen, halo, methyl, methoxy or trifluoromethyl.

9. A quinolone according to claim 1 of formula XI

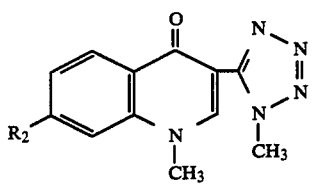

in which $R_2$ is hydrogen, halo, methyl, ethyl, methoxy or trifluoromethyl.

10. The quinolone according to claim 9 in which $R_2$ is hydrogen.

11. The quinolone according to claim 9 in which $R_2$ is methyl.

12. A pharmaceutical composition useful for effecting antihypertensive activity and vasodilation in mammals including humans which comprises an antihypertensively effective amount or a vasodilating effective amount of a quinolone of the formula I

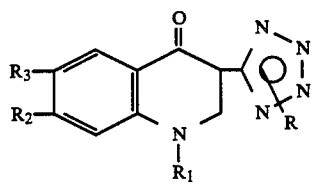

in which the dotted lines between positions 2 and 3 of the quinolone ring represents and optional bond, R is hydrogen, 1-methyl or 2-lower alkyl; $R_1$ is lower alkyl; $R_2$ is hydrogen, halo, lower alkyl, lower alkoxy, trifluoromethyl, cyano, difluoromethoxy, methylsulphinyl, phenylsulphinyl or the group $-NR_4R_5$ or the N-oxide thereof wherein $R_4$ and $R_5$ are the same or different lower alkyl; and $R_3$ is hydrogen, fluoro, lower alkyl or lower alkoxy provided that, when $R_3$ is lower alkoxy, $R_2$ is other than lower alkoxy, in combination with a pharmaceutically acceptable carrier.

13. A pharmaceutical composition according to claim 12 in which the quinolone is of the formula IX

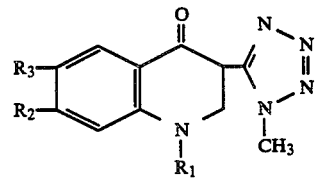

in which $R_1$ is lower alkyl, $R_2$ is hydrogen, halo, lower alkyl, lower alkoxy, trifluoromethyl, cyano or difluoromethoxy and $R_3$ is hydrogen, fluoro, lower alkyl or lower alkoxy, provided that when $R_3$ is lower alkoxy, $R_2$ is other than lower alkoxy.

14. A pharmaceutical composition according to claim 13 in which the lower alkyl and lower alkoxy moieties are of one carbon atom.

15. A pharmaceutical composition according to claim 14 in which $R_3$ is fluoro.

16. A pharmaceutical composition according to claim 14 in which $R_3$ is hydrogen.

17. A pharmaceutical composition according to claim 12 in which the quinolone is of the formula X

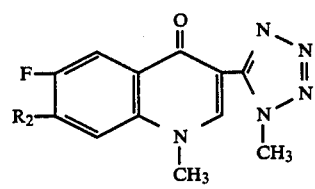

in which $R_2$ is hydrogen, halo, methyl, methoxy or trifluoromethyl.

18. A pharmaceutical composition according to claim 12 in which quinoline is of the formula XI

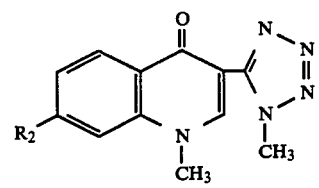

in which $R_2$ is hydrogen, halo, methyl, ethyl, methoxy or trifluoromethyl.

19. A pharmaceutical composition according to claim 18 in which $R_2$ is hydrogen.

20. A pharmaceutical composition according to claim 18 in which $R_2$ is methyl.

21. A method of treating hypertension and effecting vasodilation in mammals including humans which comprises administering to such a mammal in need thereof a therapeutically effective amount of a quinolone of the formula I

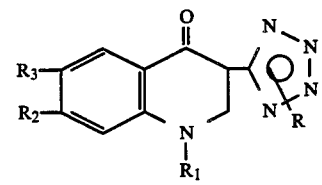

in which the dotted lines between positions 2 and 3 of the quinolone ring represents and optional bond, R is hydrogen, 1-methyl or 2-lower alkyl; $R_1$ is lower alkyl; $R_2$ is hydrogen, halo, lower alkyl, lower alkoxy, trifluoromethyl, cyano, difluoromethoxy, methylsulphinyl, phenylsulphinyl or the group $-NR_4R_5$ or the N-oxide thereof wherein $R_4$ and $R_5$ are the same or different lower alkyl; and $R_3$ is hydrogen, fluoro, lower alkyl or lower alkoxy provided that, when $R_3$ is lower alkoxy, $R_2$ is other than lower alkoxy, in combination with a pharmaceutically acceptable carrier.

22. A method according to claim 21 in which the quinolone is of the formula IX

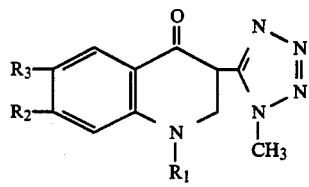

IX in which $R_1$ is lower alkyl, $R_2$ is hydrogen, halo, lower alkyl, lower alkoxy, trifluoromethyl, cyano or difluoromethoxy and $R_3$ is hydrogen, fluoro, lower alkyl or lower alkoxy, provided that when $R_3$ is lower alkoxy, $R_2$ is other than lower alkoxy.

23. A method according to claim 22 in which the lower alkyl and lower alkoxy moieties are of one carbon atom.

24. A method according to claim 23 in which $R_3$ is fluoro.

25. A method according to claim 23 in which $R_3$ is hydrogen.

26. A method according to claim 21 in which the quinolone is of the formula X

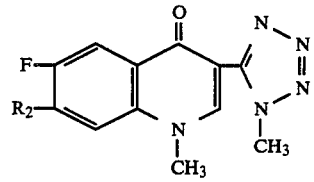

X in which $R_2$ is hydrogen, halo, methyl, methoxy or trifluoromethyl.

27. A method according to claim 21 in which the quinolone is of the formula XI

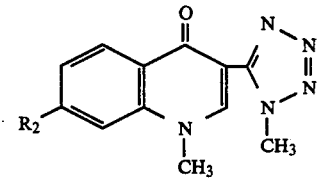

XI in which $R_2$ is hydrogen, halo, methyl, ethyl, methoxy or trifluoromethyl.

28. A method according to claim 27 in which $R_2$ is hydrogen.

29. A method according to claim 27 in which $R_2$ is methyl.

* * * * *